United States Patent
Chiang et al.

(10) Patent No.: US 8,349,371 B2
(45) Date of Patent: Jan. 8, 2013

(54) METHOD FOR ANTI-OXIDATION, INHIBITING ACTIVITY AND/OR EXPRESSION OF MATRIX METALLOPROTEINASE, AND/OR INHIBITING PHOSPHORYLATION OF MITOGEN-ACTIVATED PROTEIN KINASE USING NEONAUCLEA RETICULATA LEAF EXTRACTS

(75) Inventors: Hsiu-Mei Chiang, Taichung (TW); Kuo-Ching Wen, Taichung (TW)

(73) Assignee: China Medical University, Taichung (TW)

( * ) Notice: Subject to any disclaimer, the term of this patent is extended or adjusted under 35 U.S.C. 154(b) by 12 days.

(21) Appl. No.: 13/032,016

(22) Filed: Feb. 22, 2011

(65) Prior Publication Data

US 2012/0148694 A1 Jun. 14, 2012

(30) Foreign Application Priority Data

Dec. 14, 2010 (TW) .............................. 99143696 A

(51) Int. Cl.
*A61K 36/00* (2006.01)
(52) U.S. Cl. ....................................... 424/725; 424/774
(58) Field of Classification Search ........................ None
See application file for complete search history.

(56) References Cited

OTHER PUBLICATIONS

Revilla et al. (Comparison of Several Procedures Used for the Extraction of ANthocyanins from Red Grapes, J. Agric. Food Chem. 1998, pp. 4592-4597).*

* cited by examiner

*Primary Examiner* — Terry A. McKelvey
*Assistant Examiner* — Randall Winston
(74) *Attorney, Agent, or Firm* — Greer, Burns & Crain, Ltd.

(57) ABSTRACT

A method of inhibiting at least one selected from the group consisting of oxidation, the activity of matrix metalloproteinase (MMP), the expression of matrix metalloproteinase, and the phosphorylation of mitogen-activated protein kinase (MAP kinase) in a mammal, comprising administrating to the mammal an effective amount of a *Neonauclea reticulate* leaf extract, is provided.

15 Claims, 9 Drawing Sheets

NRW: Neonauclea reticulata water extract
EGCG: Epigallocatechin gallate

METHOD FOR ANTI-OXIDATION, INHIBITING ACTIVITY AND/OR EXPRESSION OF MATRIX METALLOPROTEINASE, AND/OR INHIBITING PHOSPHORYLATION OF MITOGEN-ACTIVATED PROTEIN KINASE USING NEONAUCLEA RETICULATA LEAF EXTRACTS

CROSS-REFERENCES TO RELATED APPLICATIONS

This application claims the benefit of Taiwan Patent Application No. 099143696, filed on Dec. 14, 2010, in the Taiwan Intellectual Property Office, the disclosure of which is incorporated herein in its entirety by reference.

BACKGROUND OF THE INVENTION

1. Field of the Invention

The present invention relates to a *Neonauclea reticulata* leaf extract and its use in anti-oxidation, in the inhibition of the activity of matrix metalloproteinase (MMP), in the inhibition of the expression of matrix metalloproteinase, and/or in the inhibition of the phosphorylation of mitogen-activated protein kinase (MAP kinase), especially in the improvement, care, and/or repair of skin.

2. Descriptions of the Related Art

Natural human aging processes include wrinkle formation, skin flaccidity and skin darkening, which gradually appear with aging. The layers of skin from top to bottom are the epidermis, dermis, and hypodermis. The causes of skin aging can be classified into endogenous and exogenous factors. Endogenous aging is a natural aging process of the human body, including cell apoptosis, hormone decrease, and weakened immunity. The decrease of hormone secretion may slow the skin metabolism and gradually reduce the production of collagen and elastin due to the deterioration of fibroblast function in the dermis.

As a result, the connective tissues in the dermis deteriorate, leading to skin flaccidity, and even wrinkling. Furthermore, the deterioration of the connective tissues in the dermis may decrease the water storage function of the skin, leading to skin dryness and water deficiency, etc.

Exogenous aging is caused by extrinsic factors, such as sunshine, pollution, free radicals, and smoking. The main factor that damages the skin most and accelerates the aging of skin is ultraviolet (UV) rays from the sun. Depending on the wavelength, ultraviolet (UV) rays can be classified into long wavelength UV (UVA), medium wavelength UV (UVB), and short wavelength UV (UVC). UV rays that people are most exposed to in daily life are UVA and UVB, which may cause erythema, sunburns, damage to the deoxyribonucleic acid (DNA) in skin cells, abnormality of the skin immune system, and skin cancer. The aging process caused by UV rays is called "photo-aging," which may increase the amount of matrix metalloproteinase (MMP) in the dermis via the phosphorylation of the mitogen-activated protein kinase (MAP Kinase) pathway. Matrix metalloproteinase may decompose collagen to reduce the collagen content in the skin. Furthermore, UV rays may promote the formation of reactive oxygen species (ROS), such as oxygen ions, peroxides, organic and inorganic radicals, etc., and cause denaturing of the collagen and loss of collagen function. Without the support of collagen, the skin becomes flaccid, and cuticula may overgrow, leading to darkened skin.

Currently known animal collagen can be classified approximately into 21 types. Different kinds of collagen exist in different tissues. Out of all collagen in skin tissues, Type I collagen is the most abundant (80% of skin collagen) and has the most functions. Type III collagen comprises about 20% of the skin collagen. Fibroblasts in the dermis mainly produce Type I collagen and Type III collagen for the skin.

As described above, matrix metalloproteinase may decompose collagen to reduce the collagen content in the skin, while reactive oxygen species will cause collagen to lose its function. Thus, if the oxidation reaction of reactive oxygen species, the MAP Kinase pathway, or the activity and/or expression of matrix metalloproteinase can be inhibited, then the effects of improving/caring for skin quality can be achieved.

It has been found that the expression of matrix metalloproteinase-1 can be inhibited by ziyuglycoside-I obtained by extracting the roots of *Sanguisorba officinalis* with 70% ethanol. The expression of matrix metalloproteinase-1 can also be inhibited by sumaflavone and amentoflavone obtained by extracting *Selaginella tamariscina* with methanol. However, there is still a need to find components that have better effects of inhibiting the activity of matrix metalloproteinase.

The inventors of the present invention discovered that a *Neonauclea reticulata* leaf extract has excellent effects of anti-oxidation, inhibiting the activity of matrix metalloproteinase, inhibiting the expression of matrix metalloproteinase, and/or inhibiting the phosphorylation of MAP Kinase. Thus, the extract can be used in the improvement, care, and/or repair of skin.

SUMMARY OF THE INVENTION

An objective of the present invention is to provide a *Neonauclea reticulata* leaf extract, wherein the absorption spectroscopy of the extract includes peaks within the following wavelength ranges: from 265 to 295 nm and from 305 to 335 nm.

Another objective of the present invention is to provide a method of inhibiting at least one selected from the group consisting of oxidation, the activity of matrix metalloproteinase (MMP), the expression of matrix metalloproteinase, and the phosphorylation of mitogen-activated protein kinase (MAP kinase) in a mammal, comprising administrating to the mammal an effective amount of a *Neonauclea reticulata* leaf extract.

Yet a further objective of the present invention is to provide a pharmaceutical composition for inhibiting at least one selected from the group consisting of oxidation, the activity of matrix metalloproteinase, the expression of matrix metalloproteinase, and the phosphorylation of mitogen-activated protein kinase, and the pharmaceutical composition comprises an effective amount of the above *Neonauclea reticulata* leaf extract.

The detailed technology and preferred embodiments implemented for the present invention are described in the following paragraphs accompanying the appended drawings for people skilled in this field to well appreciate the features of the claimed invention.

DESCRIPTION OF THE PREFERRED EMBODIMENT

Figure 1:
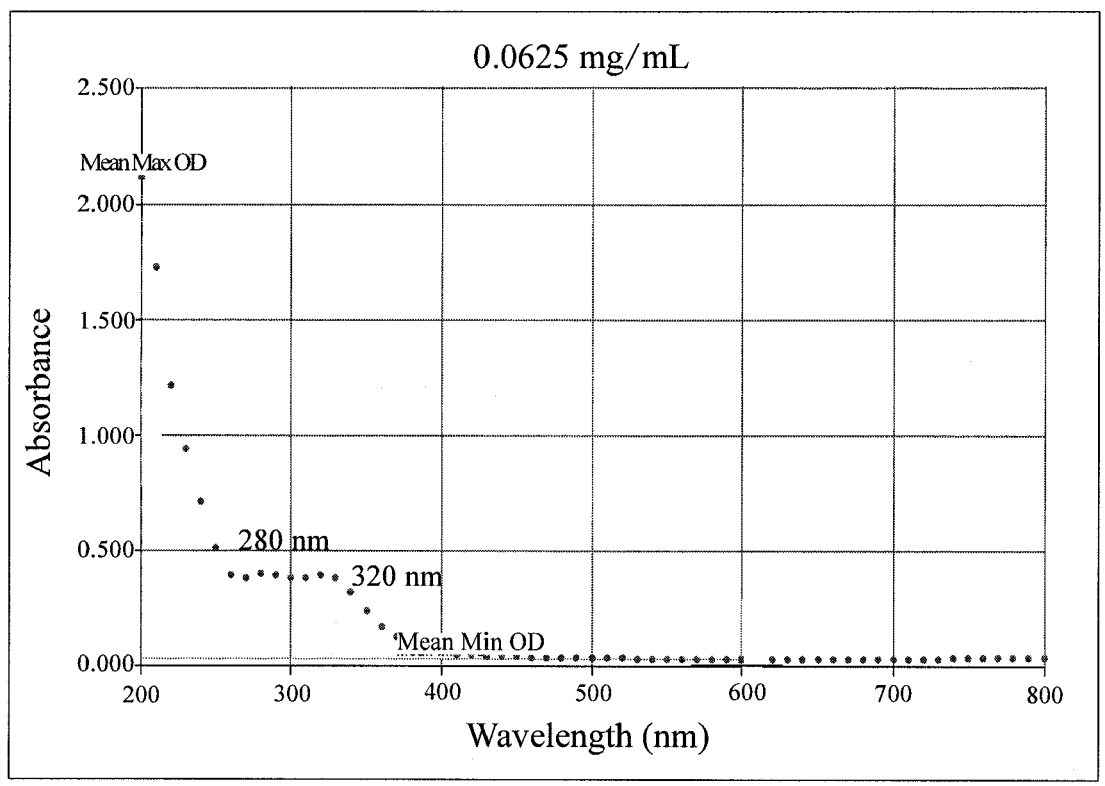
FIGS. 1 to 5 are UV-VIS spectrograms of the *Neonauclea reticulata* leaf extract of the present invention.
Figure 2:
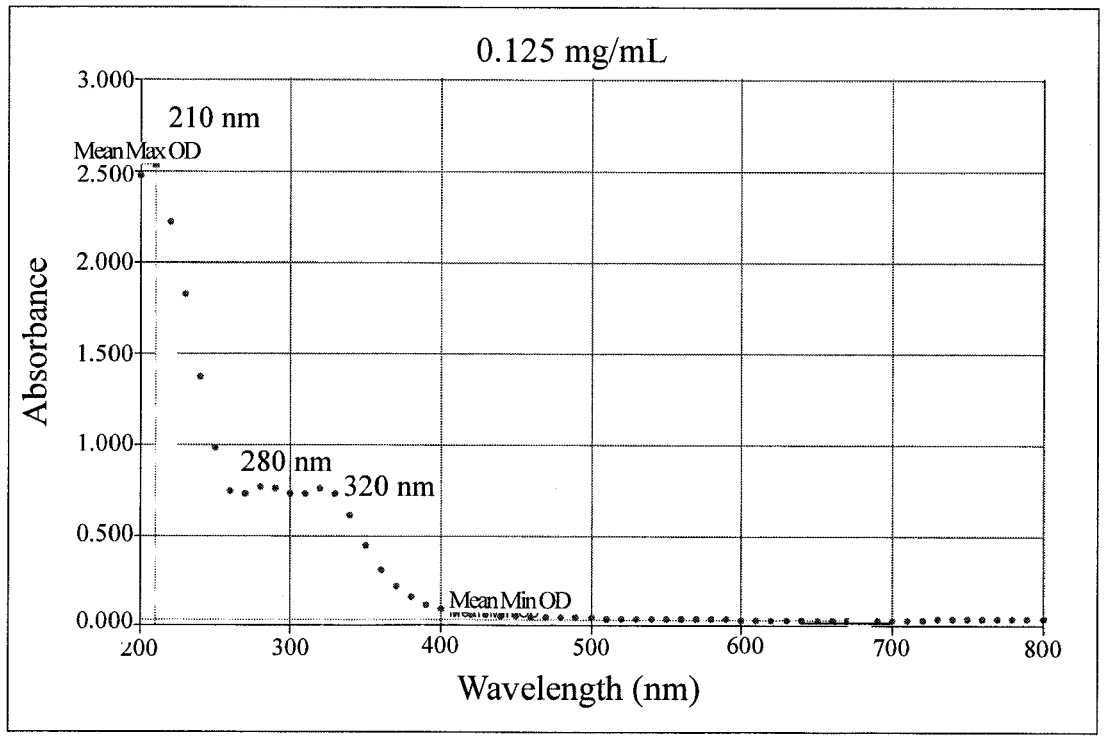
Figure 3:
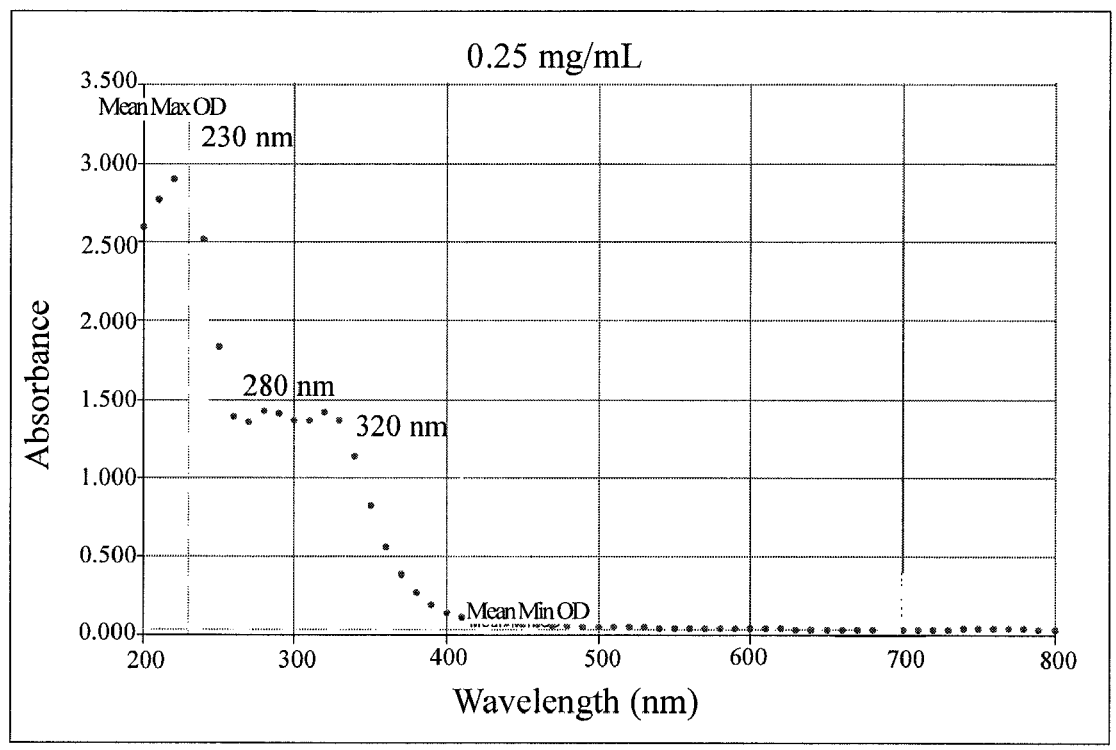
Figure 4:
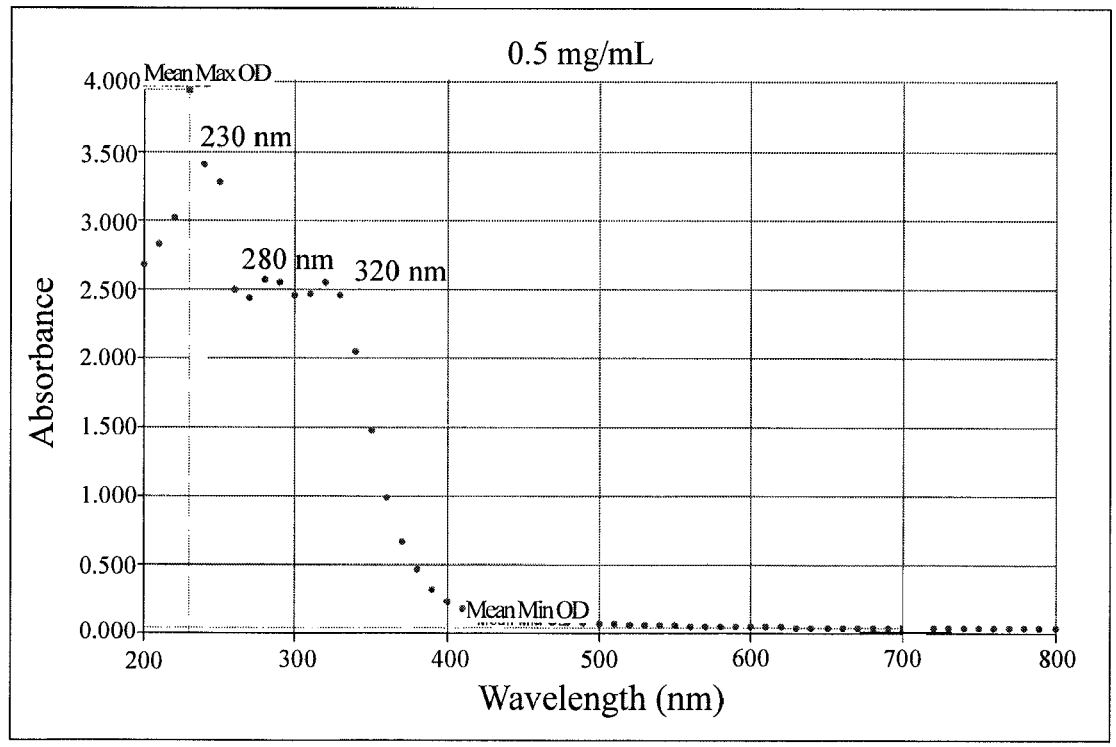
Figure 5:
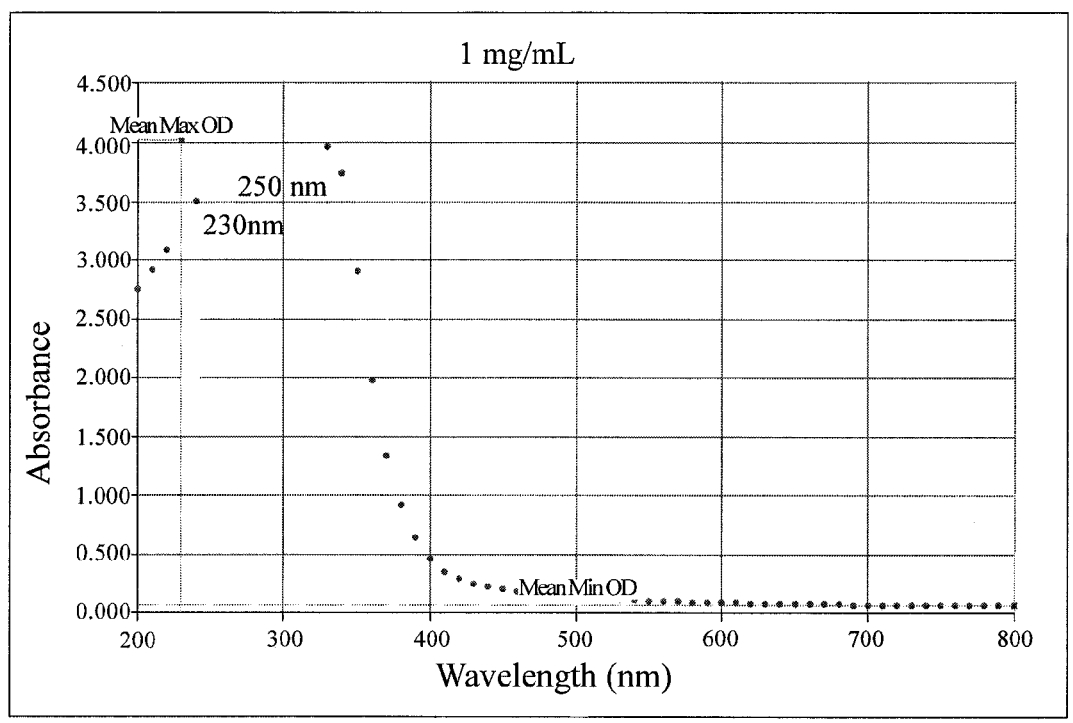

Unless otherwise stated herein, the terms "a (an)," "the" or the like used in this specification (especially in the Claims hereinafter) shall be understood to encompass both the singular form and the plural form.

The present invention relate to a method of inhibiting at least one selected from the group consisting of oxidation, the activity of matrix metalloproteinase (MMP), the expression of matrix metalloproteinase, and the phosphorylation of mitogen-activated protein kinase (MAP kinase) in a mammal, comprising administrating to the mammal an effective amount of a *Neonauclea reticulata* leaf extract to the mammal. The absorption spectroscopy of the *Neonauclea reticulata* leaf extract includes peaks within the following wavelength ranges: from 265 to 295 nm and from 305 to 335 nm. In one embodiment of the present invention, the absorption spectroscopy of the *Neonauclea reticulata* leaf extract includes peaks within the following wavelength ranges: from 200 to 240 nm, from 245 to 255 nm, from 270 to 290 nm, and from 310 to 330 nm.

The *Neonauclea reticulata* leaf extract of the present invention has effects of inhibiting the activity of matrix metalloproteinase and inhibiting the expression of matrix metalloproteinase, and may prevent or decrease the destruction of collagen. Matrix metalloproteinase can be classified as collagenase, stromelysin, gelatinase, matrilysin, transmembrane type-MMP, etc. In particular, the *Neonauclea reticulata* leaf extract of the present invention can effectively inhibit the formation (or expression) of matrix metalloproteinase-1 (MMP-1), matrix metalloproteinase-3 (MMP-3), and matrix metalloproteinase-9 (MMP-9). MMP-1 is also called collagenase-1, which belongs to the collagenase family. Other names for MMP-1 include tissue collagenase or fibroblast-type collagenase. MMP-3 is also called stromelysin-1, which belongs to the stromelysin family, substrates of which include fibronectin, laminin, and non-fibrillar collagen. MMP-9 belongs to the gelatinase family, a major substrate of which is Type IV collagen. Without being limited by theory, it is believed that the *Neonauclea reticulata* leaf extract of the present invention can indirectly increase the formation of collagen by inhibiting the activity and/or expression of matrix metalloproteinase.

Apart from effectively inhibiting the activity and/or expression of matrix metalloproteinase, the extract of the present invention also can inhibit the phosphorylation of mitogen-activated protein kinase (MAP kinase). In particular, it can inhibit the phosphorylation of c-Jun N-terminal Kinase (JNK), the extracellular signal-regulated protein kinase (ERK), and p38 protein. The phosphorylation of MAP kinase would increase the amount of matrix metalloproteinase in the dermis, therefore increasing the opportunity of collagen degradation and decreasing the collagen content in skin.

In addition, the *Neonauclea reticulata* leaf extract of the present invention also has anti-oxidation effects. As described above, the oxidation of reactive oxygen species can denature the collagen and cause it to lose function, and thus collagen can no longer support the skin, leading to skin flaccidity and darkening.

Because the *Neonauclea reticulata* leaf extract of the present invention simultaneously has the effects of (1) inhibiting the activity and/or expression of matrix metalloproteinase; (2) indirectly inhibiting the expression of matrix metalloproteinase by suppressing the phosphorylation of mitogen-activated protein kinase; and (3) inhibiting the oxidation reaction of reactive oxygen species, it greatly reduces collagen decomposition and denaturing in the skin, and may effectively improve, repair, and/or care for skin. For example, the extract may achieve the effects of anti-aging, anti-photoaging, reducing skin wrinkles, improving skin quality and skin flaccidity, promoting wound healing, etc.

The *Neonauclea reticulata* leaf extract of the present invention can be prepared by a method comprising the following steps: a) extracting *Neonauclea reticulata* leaves with a solvent and collecting the liquid phase; and optionally b) drying the collected liquid phase. The solvent (i.e., the extraction solvent) that can be used is selected from a group consisting of water, alcohols, and combinations thereof. Preferably, the solvent is selected from a group consisting of water, $C_1$-$C_4$ alcohols, and combinations thereof More preferably, the solvent is selected from a group consisting of water, methanol, ethanol, propanol, butanol, propylene glycol, and combinations thereof Most preferably, the solvent is selected from a group consisting of water, methanol, and a combination thereof. The weight ratio of the extraction solvent and *Neonauclea reticulata* leaves is not a key factor in the present invention, and usually is about 10:1 to about 50:1, and preferably about 20:1 to about 40:1.

Optionally, before step a), *Neonauclea reticulata* leaves to be extracted are dried and ground to promote the effectiveness of the extraction. In step a), the extraction is carried out for a period of time to achieve the desired extraction efficiency. For example, when methanol is used as the extraction solvent, the extraction time is usually at least 30 minutes, more preferably at least 60 minutes, and most preferably at least 90 minutes. The extraction may be optionally assisted with other appropriate extracting approaches (e.g., ultrasonic vibration, heating, etc.) to increase extraction efficiency. In addition, prior to step b), the extraction in step a) may be optionally repeated one or more times, and all of the liquid phase are combined to provide a liquid phase for step b) to separate the active components from the inactive components in *Neonauclea reticulata* leaves as much as possible to reduce resource waste and benefit the economy.

In general, depending on the application of the *Neonauclea reticulata* leaf extract, a drying step may be optionally carried out to dry the *Neonauclea reticulata* leaf extract liquid obtained in step a). For example, if the selected extraction solvent is methanol or ethanol, either of which is not irritating to the skin, and the obtained *Neonauclea reticulata* leaf extract liquid is to be applied to the skin directly, additional drying for the extract liquid is not needed. However, if the *Neonauclea reticulata* leaf extract of the present invention is to be applied by oral administration, a drying step (such as freeze drying, concentrating under a vacuum condition, and/or ventilation) can be used to remove the organic solvents in the *Neonauclea reticulata* leaf extract to prevent the organic solvents from harming the body.

An acid hydrolysis may be proceeded after step a) or the optional step b) (when step b) is carried out) to obtain the hydrolyte of the *Neonauclea reticulata* leaf extract. Therefore, the method for preparing the *Neonauclea reticulata* leaf extract in the present invention can further comprise the following steps: step c) adding an acid into the liquid phase from step a) or into the dried liquid phase from optional step b) to provide a mixture and maintaining the mixture at a temperature ranging from 70° C. to 90° C. to carry out a hydrolysis reaction; d) partitioning the product from step c) with ethyl acetate and collecting the ethyl acetate layer; and optionally e) drying the collected ethyl acetate layer. The acid used in step c) can be selected from a group consisting of hydrochloric acid, sulfuric acid, and a combination thereof, and the equivalent concentration (N) of the acid can be from 0.3 to 2.0. For example, hydrochloric acid with an equivalent concentration of 0.5 to 1.5 can be used for the hydrolysis.

In one embodiment of the present invention, the finely ground powder of *Neonauclea reticulata* leaves were extracted with methanol or water and soaked therein to obtain an extract liquid, and the weight ratio of methanol or water to the *Neonauclea reticulata* leaves was about 30:1. The extract liquid was then concentrated under a vacuum condition to obtain a dried *Neonauclea reticulata* leaf extract.

The present invention also relates to a pharmaceutical composition for anti-oxidation, inhibiting the activity of matrix metalloproteinase, inhibiting the expression of matrix metalloproteinase, and/or inhibiting the phosphorylation of mitogen-activated protein kinase, comprising an effective amount of the *Neonauclea reticulata* leaf extract of the present invention. Specifically, the *Neonauclea reticulata* leaf extract of the present invention can be administrated as a medicament. Based on the effects of anti-oxidation, inhibiting the activity of matrix metalloproteinase, inhibiting the expression of matrix metalloproteinase, and/or inhibiting the phosphorylation of mitogen-activated protein kinase of the pharmaceutical composition of the present invention, the pharmaceutical composition t can be particularly used for improving, repairing, and/or caring for the skin.

The pharmaceutical composition of the present invention can be of any suitable form without particular limits. For example, the pharmaceutical composition can be in a form of emulsion, cream or gel for external use, such as a skin care product, cosmetic, etc. The pharmaceutical composition can also be prepared in the form of food for swallowing or drinking, such as health foods, beauty drinks, etc. Furthermore, the pharmaceutical composition can also be of a common pharmaceutical form, such as a tablet, a capsule, a granule, a powder, a fluid extract, a solution, a syrup, a suspension, an emulsion, a tincture, an intravenous injection, a powder injection, a suspension injection, and a powder-suspension injection, etc.

The content of the *Neonauclea reticulata* leaf extract in the pharmaceutical composition of the present invention may be adjusted according to the age of the treated subject and the purpose of the application (such as reducing skin wrinkles or promoting wound healing). The usage frequency may also be optionally adjusted. For example, when the *Neonauclea reticulata* leaf extract is used for reducing skin wrinkles, the content of the *Neonauclea reticulata* leaf extract in the pharmaceutical composition usually ranges from about 0.03 wt % to about 0.4 wt %, and preferably ranges from about 0.05 wt % to about 0.25 wt %, based on the total weight of the pharmaceutical composition. The other components and content thereof are dependent on the final form of the pharmaceutical composition. For instance, when the pharmaceutical composition is prepared as a skin care product, any suitable and appropriate amount of emulsifying agent, perfume, and other active components for improving skin quality may be added therein. When the pharmaceutical composition is prepared as a tablet, an appropriate excipient can be used. In general, any component can be added to the pharmaceutical composition as long as it has no adverse influence on the desired effects of the *Neonauclea reticulata* leaf extract.

The detailed technology and preferred embodiments implemented for the subject invention are described in the following paragraphs accompanying the appended drawings for people skilled in this field to well appreciate the features of the claimed invention. However, the scope of the present invention is not limited thereby.

[Preparation of the *Neonauclea Reticulata* Leaf Extract]

*Neonauclea reticulata* leaves illustrated in the following examples for the present invention were from the central area of Taiwan. First, dried *Neonauclea reticulata* leaves were ground and added into methanol or water with a 30-fold weight corresponding to the weight of the leaves. After being soaked and ultrasound vibrated for 1 hour, the leaves were filtered with a Büchner funnel to obtain a filtrate. The filtered residues were added into 30-fold weighted methanol or water again, and ultrasound vibrated for 1 hour, and then filtered with a Büchner funnel to obtain another filtrate. Then, these two filtrates were combined and concentrated under vacuum drying at a temperature ranging from 30° C. to 40° C., and the *Neonauclea reticulata* leaf extract of the present invention was then obtained. A UV-VIS Spectrophotometer (UV-160, Shimadzu) was used to detect the characteristic absorption wavelength of the extract. The UV-VIS absorption spectra are shown in FIGS. 1 to 5 (the concentration of the *Neonauclea reticulata* leaf extract is from 0.0625 mg/mL to 1 mg/mL).

Next, hydrochloric acid with the equivalent concentration (N) of 0.6 or 1.2 each was added into the *Neonauclea reticulata* leave extract, then heated in a water bath at 70° C. to 90° C. After reacting for 0.5 hour or 1 hour later, the extract hydrolyzed by hydrochloric acid was collected. The product was then partitioned with ethyl acetate, and then the ethyl acetate layer was collected and concentrated under vacuum drying to obtain the acid hydrolyte of the *Neonauclea reticulata* leaf extract.

EXAMPLE 1

Experiment A. Inhibition Test of Collagenase Activity

An agar gel (agar gel medium) was used in this experiment to evaluate the inhibition effect of the *Neonauclea reticulata* leaf extract on collagenase.

In an eppendorf tube, 50 μL of a 10-fold diluted buffer solution (prepared by mixing 5 mL of 1 M Tris (pH 7.8), 1 mL of 1 M CaCl$_2$, 3.75 mL of 4M NaCl, and 0.25 mL water), 30 μL of the distilled water, 10 μL (1 mg/mL) of the *Neonauclea reticulata* leaf methanol extract or water extract or hydrolytes thereof, and 10 μL of a bacterial collagenase (100 μg/mL, a multiple-functional collagenase obtained by gene recombination) were added and mixed evenly, and placed at room temperature for 1 hour. The mixed solution (40 μL) was added onto a filter paper on an agar gel medium and placed in an incubator at 37° C. to react for 18 hours. Afterwards, the filter paper was removed, and the medium was stained with a staining agent for 15 minutes, and then de-stained. A photograph of the medium was taken and analyzed by a TINA software (Prevx community, Germany) to calculate the inhibition rate of the *Neonauclea reticulata* leaf extract and its hydrolytes. In the experiment, propylene glycol and doxycycline were used to replace the *Neonauclea reticulata* leaf extract as a control group and a positive control group, respectively, and distilled water was used to replace collagenase for determining the background value. After the tests were independently carried out for three times, the mean value and standard deviation were calculated with the following formula. The results are shown in Table 1, Table 2, FIG. 6, and FIG. 7.

$$\text{Inhibition Rate } (\%) = \left[\frac{(C-B)}{(A-B)}\right] \times 100$$

A: a solution comprising no collagenase and the extract
B: a solution comprising collagenase, but not the extract
C: a solution comprising collagenase and the extract

TABLE 1

| Group | Propylene Glycol | Doxycycline | Methanol Extract | Water Extract |
|---|---|---|---|---|
| Inhibition Rate (%) | −19.39 ± 6.58 | 84.42 ± 7.02 | 98.69 ± 2.50 | 98.92 ± 4.16 |

Figure 6:
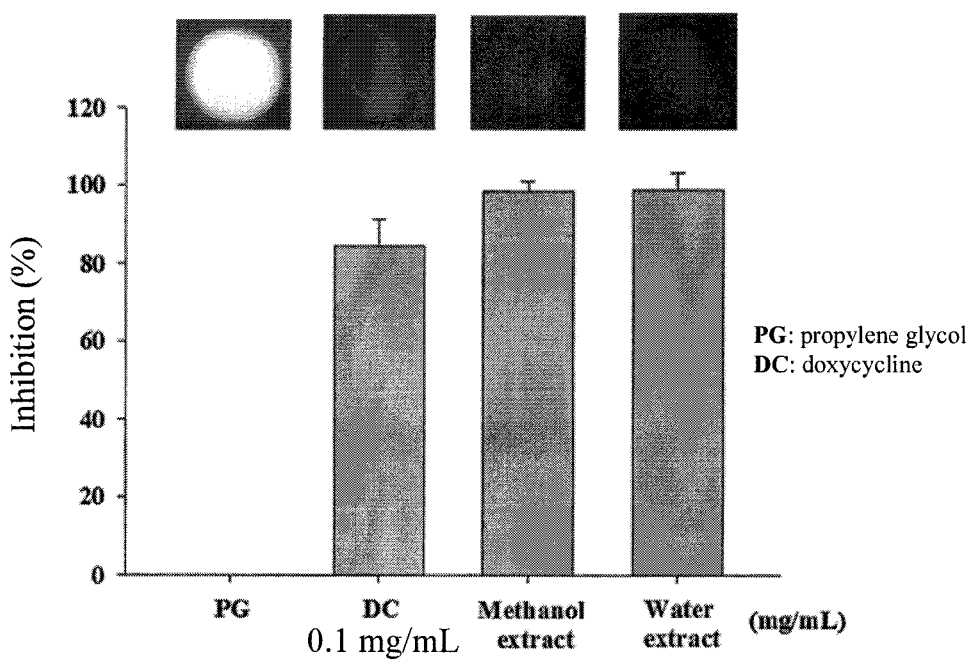
FIG. 6 is a bar diagram showing the inhibition rate of the *Neonauclea reticulata* leaf extract of the present invention on collagenase.
Figure 7:
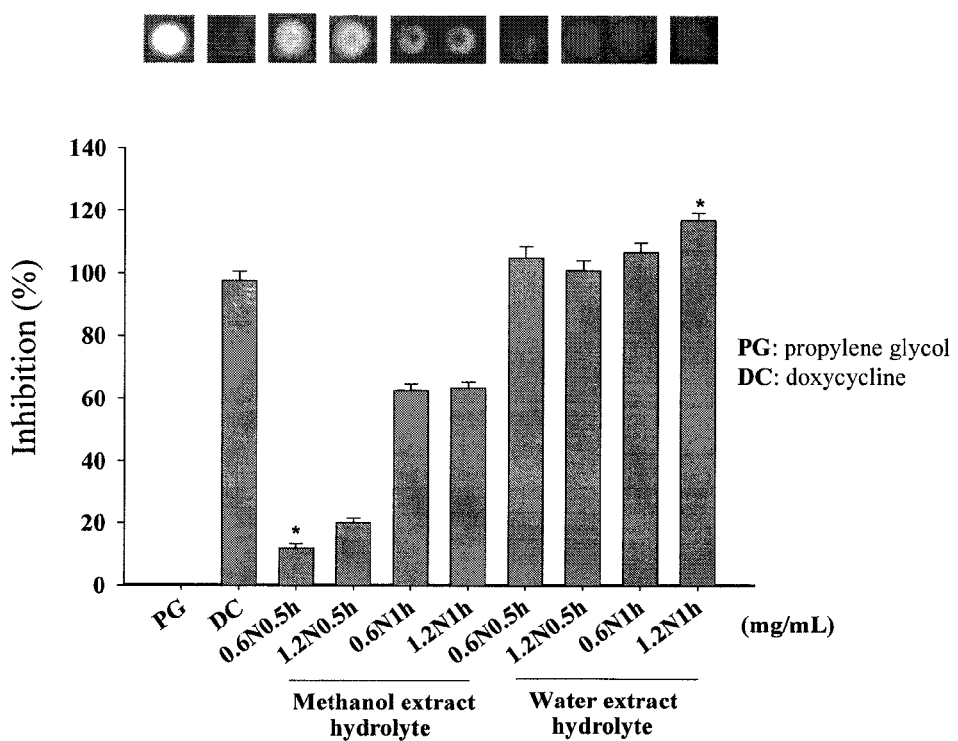
FIG. 7 is a bar diagram showing the inhibition rate of the *Neonauclea reticulata* leaf extract of the present invention on collagenase.

As shown in Table 1, Table 2, FIG. 6, and FIG. 7, the inhibition rate of the *Neonauclea reticulata* leaf extract was about 98%. This test shows that the *Neonauclea reticulata* leaf extract of the present invention can effectively inhibit the activity of collagenase. Furthermore, the test results of the acid hydrolytes of the methanol and water extracts of the *Neonauclea reticulata* leaves showed that under each reaction condition, the hydrolyte of the methanol extract is not as effective as the methanol extract itself to inhibit the collagenase. However, the hydrolyte of the water extract has similar effects as the water extract itself to inhibit the collagenase.

Experiment B. Concentration-Dependent Inhibition Test of Collagenase Activity

To further confirm the inhibition effects of the *Neonauclea reticulata* leaf extract on collagenase, the extract was diluted to various concentrations (10 to 500 μg/mL).

In an eppendorf tube, 132 μL of the distilled water, 22 μL of a 10-fold diluted buffer solution (prepared by mixing 5 mL of 1 M Tris (pH 7.8), 1 mL of 1 M CaCl$_2$, 3.75 mL of 4 M NaCl, and 0.25 mL water), 22 μL of the *Neonauclea reticulata* leaf methanol or water extract (10 to 500 μg/mL), 22 μL of a bacterial collagenase (100 mg/mL), and 22 μl of a fluorogenic substrate (fluorogenic peptide substrate I of collagenase) solution were added and mixed evenly, and placed in an incubator at 37° C. to react for 20 hours. Then, 200 μL of the reacted solution was placed into a 96-well microplate. The fluorescent strength of the solution was tested under a 320 nm exciting light and a 405 nm radiation light by an enzyme immunoassay instrument. In the experiment, propylene glycol and doxycycline were used to replace the *Neonauclea reticulata* leaf extract as a control group and a positive control group, respectively, and collagenase and the fluorogenic substrate were replaced by distilled water for determining the background value. After the tests were independently carried out three times, the mean value and standard deviation were calculated with the following formula.

Figure 8:
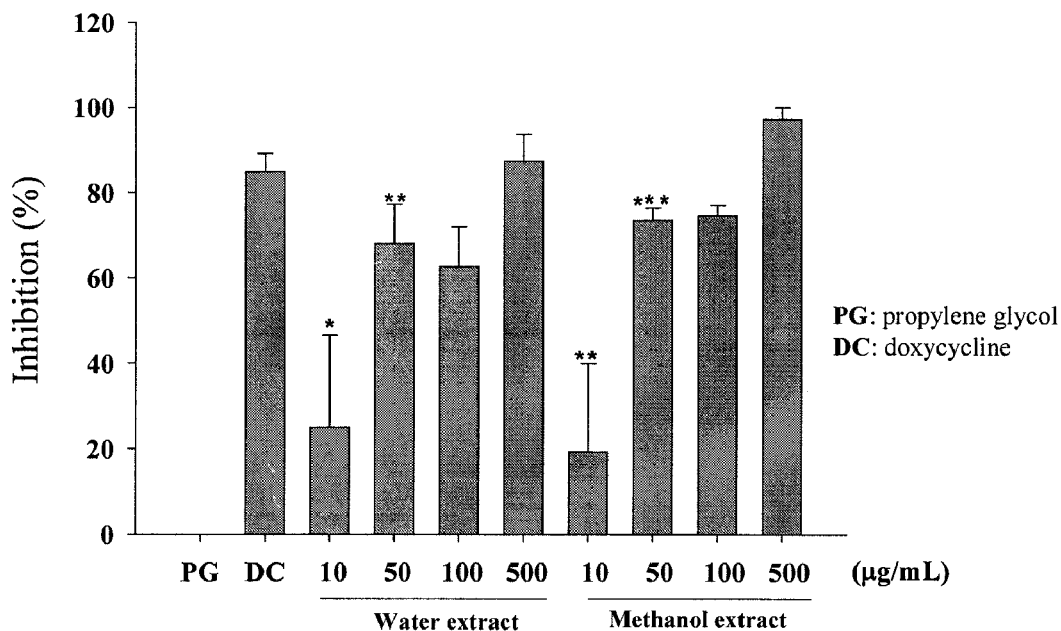
FIG. 8 is a bar diagram showing the inhibition rate of the *Neonauclea reticulata* leaf extract of the present invention on collagenase.

The results are shown in Table 3 and FIG. 8.

$$\text{Inhibition Rate } (\%) = \left[\frac{\text{Absorption value of the control group} - \text{Absorption value of the experiment group}}{\text{Absorption value of the control group}}\right] \times 100$$

TABLE 2

| Group | | Inhibition Rate |
|---|---|---|
| Propylene Glycol | | −3.64 ± 1.42 |
| Doxycycline | | 97.70 ± 2.94 |
| Hydrolyte of Methanol Extract | 0.6 N, 0.5 hour | 12.05 ± 1.36 * |
| | 1.2 N, 0.5 hour | 20.20 ± 1.37 |
| | 0.6 N, 1 hour | 62.71 ± 2.07 |
| | 1.2 N, , 1 hour | 63.47 ± 1.95 |
| Hydrolyte of Water Extract | 0.6 N, 0.5 hour | 104.94 ± 3.60 |
| | 1.2 N, 0.5 hour | 100.97 ± 3.16 |
| | 0.6 N, 1 hour | 106.70 ± 3.21 |
| | 1.2 N, 1 hour | 117.10 ± 2.33 * |

Compared to the control group, * P < 0.05

TABLE 3

| Group | | Inhibition Rate |
|---|---|---|
| Propylene Glycol | | 0 ± 29.20 |
| Doxycycline | | 84.91 ± 4.17 |
| Methanol Extract | 10 (μg/mL) | 24.95 ± 21.58 * |
| | 50 (μg/mL) | 68.03 ± 9.29 ** |
| | 100 (μg/mL) | 62.56 ± 9.36 |
| | 500 (μg/mL) | 87.25 ± 6.31 |
| Water Extract | 10 (μg/mL) | 19.21 ± 20.66 ** |
| | 50 (μg/mL) | 73.49 ± 2.84 *** |
| | 100 (μg/mL) | 74.46 ± 2.55 |
| | 500 (μg/mL) | 97.15 ± 2.78 |

Compared to the control group, * P < 0.05,  P < 0.01, * P < 0.001.

As shown in Table 3 and FIG. 8, the inhibition effect of the *Neonauclea reticulata* leaf methanol and water extract on collagenase was concentration-dependent, and the extracts had an excellent inhibition effect on collagenase. Even under the concentration of 500 µg/mL, the extracts reached the same effect as doxycycline to inhibit collagenase.

EXAMPLE 2

Experiment C. Inhibition Test of Matrix Metalloproteinase Expression

A total of $5 \times 10^5$ fibroblast Hs68 (human foreskin fibroblast, Bioresource Collection and Research Center (BCRC) number:60038, purchased from Food Industry Research and Development Institute (FIRDI)) was counted and cultivated in a culture medium (90% Dulbecco's modified Eagle's medium adjusted with 4 mM of L-glutamine, containing 1.5 g/L $NaHCO_3$, 4.5 g/L glucose, and 10% heat-inactivated fetal bovine serum) with a diameter of 10 cm. After the fibroblast Hs68 grew to a density of 80%, the culture solution was removed, and the cells were rinsed with 5 mL of a phosphate buffer saline (PBS) solution once. Then, 3 mL of a phenol red-free culture solution containing the *Neonauclea reticulata* leaf water extract with different concentrations (0 to 50 mg/mL) was added into the culture medium, and was reacted for 1 hour. The cells were placed under ultraviolet light (40 $mJ/cm^2$, Ultraviolet B (UVB)) for irradiation. Afterwards, 7 mL of a phenol red-free culture solution containing the *Neonauclea reticulata* leaf water extract with different concentrations (0 to 50 mg/mL) was further added into the culture medium, and the cells were cultured in an incubator at 37° C. containing 5 vol % carbon dioxide for 48 hours, and then the cells were collected.

A lysing buffer solution (comprising 100 mM $Na_3VO_4$, 100 mg/mL Phenylmethanesulfonyl fluoride (PMSFL), 20 mg/mL Leupeptin, 50 mM Tris-HCl with pH 7.4, 37.5 mM NaCl, 250 mM DL-dithiothreitol, 3 mM of Sodium deoxycholate, 1 mM EDTA, 0.1% SDS, and 1% IgepalTM CA-630 (purchased from Sigma-Aldrich)) was used to treat the collected cells. An additional physical vibration was applied to break the cell membranes, and the cell organelles and fragments were precipitated by a centrifuge. The supernatant containing cytoplasm proteins was collected. The collected proteins were separated by SDS-PAGE gel electrophoresis and were transferred to a membrane by western blotting. Based on the antigen-antibody principle, antibodies were used to detect target proteins, including Type I pro-collagen, MMP-1, MMP-3, MMP-9, and β-actin. Using luminescence imaging technology with an associated analysis software and LAS-4000 (FUJIFILM) to record the image, and a quantitative analysis was carried out by multi Gauge V2.2 (Steware Technology Inc.) to test the variation of the expression of the target proteins. The results are shown in Table 4, FIG. 9, and FIG. 10.

TABLE 4

| Group | Type I Collagenase | MMP-1 | MMP-3 | MMP-9 |
|---|---|---|---|---|
| Control Group | 1.00 ± 0.00 | 1.00 ± 0.00 | 1.00 ± 0.00 | 1.00 ± 0.00 |
| UV Radiation Group | 0.13 ± 0.02 | 3.15 ± 1.28* | 2.23 ± 0.39** | 1.55 ± 0.24* |
| Extract 5 µg/mL | 0.12 ± 0.01 | 1.59 ± 0.22* | 1.35 ± 0.12** | 1.26 ± 0.24 |

TABLE 4-continued

| Group | Type I Collagenase | MMP-1 | MMP-3 | MMP-9 |
|---|---|---|---|---|
| Extract 10 µg/mL | 0.20 ± 0.01 | 1.22 ± 0.32* | 1.34 ± 0.14* | 1.06 ± 0.13 |
| Extract 25 µg/mL | 0.14 ± 0.01 | 1.10 ± 0.20 | 1.29 ± 0.36 | 0.86 ± 0.26 |
| Extract 50 µg/mL | 0.19 ± 0.03 | 1.50 ± 0.33* | 1.28 ± 0.37 | 0.44 ± 0.02*** |
| EGCG 10 µg/mL | 0.00 ± 0.00 | 1.10 ± 0.15 | 1.15 ± 0.16 | 0.95 ± 0.26 |

Compared to the control group, *P < 0.05, P < 0.01, *P < 0.001.

Figure 9:
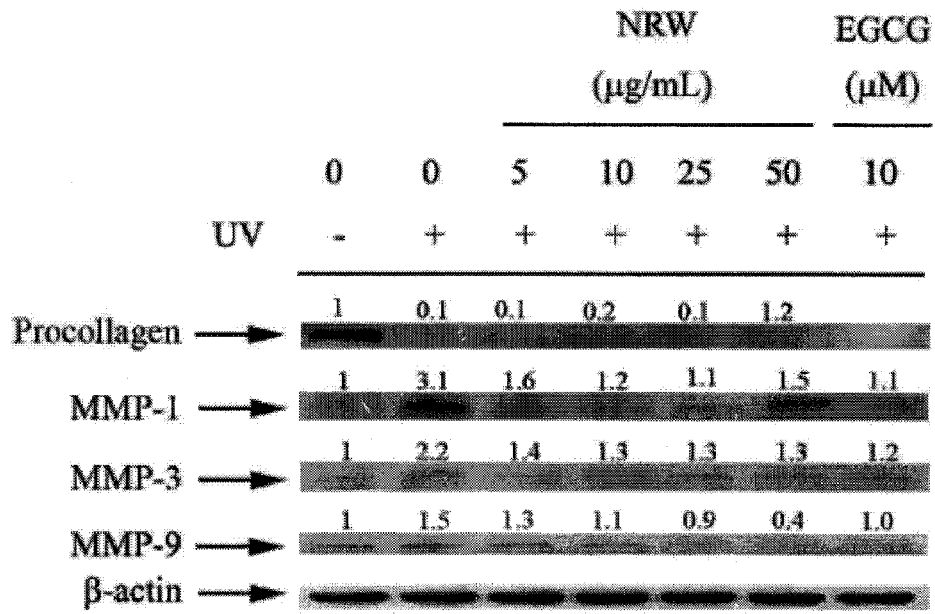
FIG. 9 is a protein electrophoresis picture of matrix metalloproteinase (MMP-1, MMP-3, and MMP-9) and Type I pro-collagen in fibroblast Hs68.
Figure 10:
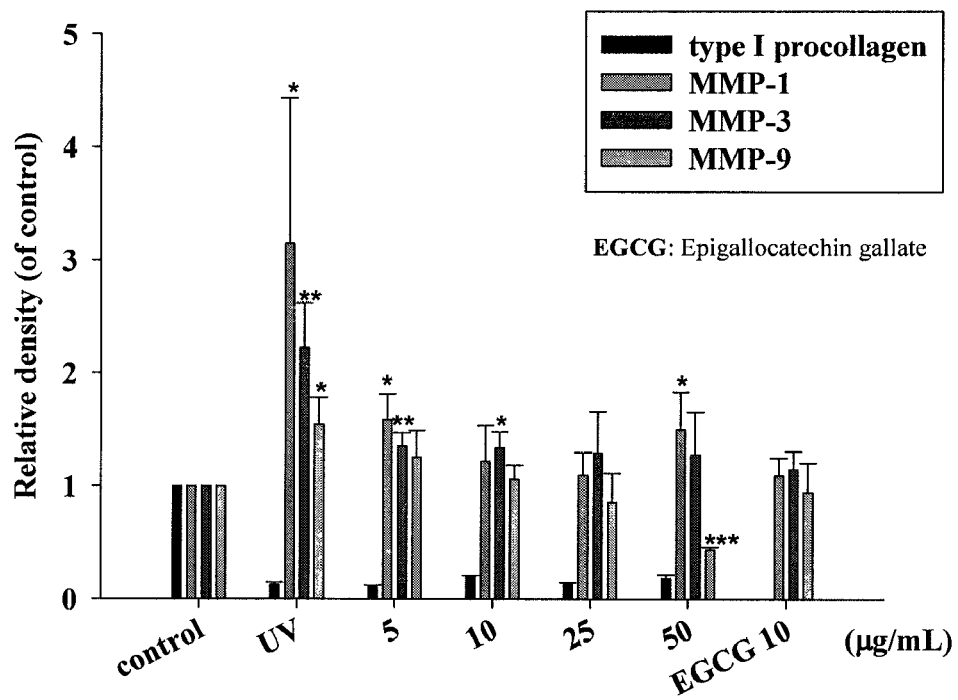
FIG. 10 is a bar diagram showing the inhibition rate of the *Neonauclea reticulata* leaf extract of the present invention on metalloproteinase (MMP-1, MMP-3, and MMP-9)

As shown in Table 4, FIG. 9, and FIG. 10, after UV light radiation, the expression amount of MMP-1, MMP-3, and MMP-9 in the fibroblasts increased to 3.1-fold, 2.2-fold, and 1.5-fold, respectively, and the expression of collagen decreased. After UV light radiation, the fibroblasts were further treated by the *Neonauclea reticulata* leaf water extract. Under the concentration of 25 and 50 µg/mL of the extract, the expression of MMP-1 and MMP-9 was inhibited, and MMP-1 expression decreased significantly from 3.1-fold to 1.1-fold, and the expression of MMP-9 decreased from 1.5-fold to 0.4-fold. The expression of MMP-3 showed similar inhibiting effect in the concentration ranging from 10 to 50 µg/mL.

The result showed that the *Neonauclea reticulata* leaf extract can effectively inhibit the expression of matrix metalloproteinase to reduce the degradation of collagenase.

EXAMPLE 3

Experiment D. Inhibition Test of Mitogen-Activated Protein Kinase Phosphorylation First, the fibroblast (human foreskin fibroblast, Bioresource Collection and Research Center (BCRC) number: 60038, purchased from Food Industry Research and Development Institute (FIRDI)) was cultivated in a culture medium (90% Dulbecco's modified Eagle's medium adjusted with 4 mM of L-glutamine, containing 1.5 g/L $NaHCO_3$, 4.5 g/L glucose, and 10% heat-inactivated fetal bovine serum). After the fibroblast grew to a density of 80%, the culture solution was changed to a culture solution containing different concentrations (0 to 100 µg/mL, dissolved in DMSO) of the *Neonauclea reticulata* leaf extract, and the cells were cultivated for 15 mins. Then, the culture solution was removed, and the fibroblast cells were rinsed twice with the phosphate buffer saline (PBS) solution. The PBS solution was then added into the culture medium. After the cells were irradiated under ultraviolet light (40 $mJ/cm^2$, Ultraviolet B (UVB)), the PBS solution was removed, and then a culture solution comprising no serum was added, and the fibroblast cells were further cultivated. The proteins within the fibroblast cells were collected after 24 hours, and the expression of unphosphorylated and phosphorylated mitogen-activated protein kinases (JNK, ERK, and p38 protein) within the fibroblast cells were observed by the Western-blotting method.

After the fibroblast cells were irradiated with short wavelength UV, the mitogen-activated protein kinase (MAPK) was induced to undergo phosphorylation, and the MAPK pathway is activated, therefore triggering the photo-aging.

Figure 11:
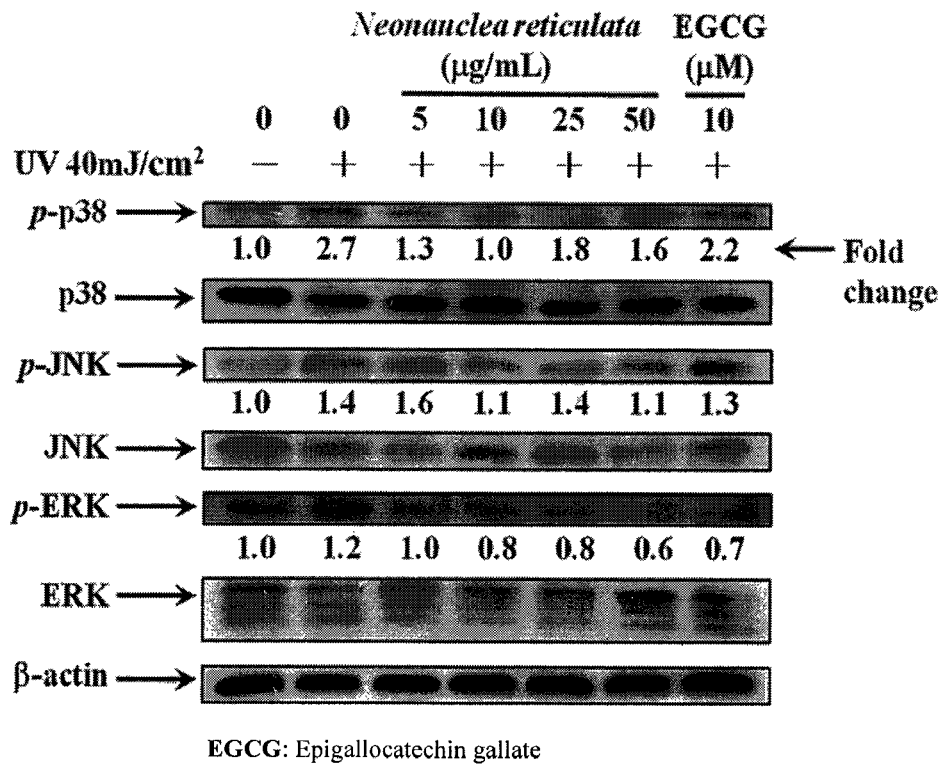
FIG. 11 is a protein electrophoresis picture of unphosphorylated and phosphorylated mitogen-activated protein kinase (JNK, ERK, and p38 protein) in fibroflast.

As shown in FIG. 11, after the fibroblast cells were irradiated by short wavelength UV, the expression amount of phosphorylated ERK, JNK, and p38 was 1.4, 1.2, and 1.5-fold, respectively, compared to the non-irradiated control group. After the cells were treated with the *Neonauclea reticulata* leaf extract, the phosphorylation of ERK was inhibited under the concentration of 10 μg/mL, and the phosphorylated amount thereof decreased from 1.4-fold to 1.1-fold. The phosphorylation of JNK decreased from 1.2-fold to 1.1-fold under the concentration of 25 μg/mL, and the phosphorylation of p38 decreased from 1.5-fold to 1-fold in the concentration of 5 μg/mL.

This example indicates that the *Neonauclea reticulata* leaf extract of the present invention can effectively inhibit the phosphorylation of mitogen-activated protein kinase, and therefore can inhibit photo-aging.

EXAMPLE 4

Experiment E. Anti-Oxidation Tests—Free Radicals Removal Test

DPPH (1, 1-diphenyl-2-picrylhydrazyl) was used as the source of free radicals to test the ability of the *Neonauclea reticulata* leaf extract to remove free radicals. A 100 μL of the *Neonauclea reticulata* leaf water extract, methanol extract, or the hydrolytes thereof with different concentrations (10 to 100 μg/mL) and a 100 μL. DPPH solution (200 μM) dissolved in methanol were added in a 96-well microplate, and were mixed evenly and placed under 37° C. away from light for 30 minutes. The absorbance of the mixture was determined by an enzyme immunoassay instrument under a wavelength of 517 nm. In this test, the extract was replaced by 50 vol % propylene glycol as the control group, and ascorbic acid (vitamin C) was used as a positive control group, and DPPH was replaced by methanol for determining the background value. The ability of the *Neonauclea reticulata* leaf extract to remove free radicals was calculated by the following formula. The results are shown in Table 5 to Table 7 and FIG. 12 to FIG. 14.

$$\text{Clearance efficiency (\%)} = \frac{\left[\begin{array}{l}(\text{Absorption value of the control group} - \text{Absorption value of the blank group}) - \\ (\text{Absorption value of the experiment group} - \text{Absorption value of the blank group})\end{array}\right]}{(\text{Absorption value of the control group} - \text{Absorption value of the blank group})} \times 100$$

TABLE 5

| Group | | Inhibition |
|---|---|---|
| Vitamin C (50 μg/mL) | | 98.60 ± 0.32 |
| Methanol Extract | 10 μg/mL | 26.58 ± 2.33** |
| | 25 μg/mL | 65.93 ± 1.20 |
| | 50 μg/mL | 95.67 ± 0.44* |
| | 75 μg/mL | 97.06 ± 0.24*** |
| | 100 μg/mL | 96.99 ± 0.50*** |
| Water Extract | 10 μg/mL | 47.07 ± 0.78*** |
| | 25 μg/mL | 82.18 ± 0.86*** |
| | 50 μg/mL | 96.33 ± 0.21* |
| | 75 μg/mL | 95.60 ± 0.21** |
| | 100 μg/mL | 97.17 ± 0.55** |

Compared to the control group, *P < 0.05, P < 0.01, *P < 0.001.

TABLE 6

| Group | | Inhibition Rate |
|---|---|---|
| Vitamin C (50 μg/mL) | | 88.36 ± 2.71 |
| 0.6 N, 0.5 hour | 10 μg/mL | 14.17 ± 1.91*** |
| | 50 μg/mL | 34.99 ± 2.87*** |
| | 100 μg/mL | 49.44 ± 4.42*** |
| 1.2 N, 0.5 hour | 10 μg/mL | 10.66 ± 2.35*** |
| | 50 μg/mL | 26.06 ± 4.59*** |
| | 100 μg/mL | 42.24 ± 2.78*** |

TABLE 6-continued

| Group | | Inhibition Rate |
|---|---|---|
| 0.6 N, 1 hour | 10 μg/mL | 9.32 ± 2.54*** |
| | 50 μg/mL | 45.81 ± 3.22*** |
| | 100 μg/mL | 72.32 ± 5.44** |
| 1.2 N, 1 hour | 10 μg/mL | 13.00 ± 3.01*** |
| | 50 μg/mL | 41.07 ± 2.66*** |
| | 100 μg/mL | 62.72 ± 2.92*** |

Compared to the control group, *P < 0.05, P < 0.01, *P < 0.001.

TABLE 7

| Group | | Inhibition Rate |
|---|---|---|
| Vitamin C (50 μg/mL) | | 97.99 ± 0.12 |
| 0.6 N, 0.5 hour | 10 μg/mL | 78.10 ± 3.10*** |
| | 50 μg/mL | 99.39 ± 1.27* |
| | 100 μg/mL | 109.92 ± 1.34*** |
| 1.2 N, 0.5 hour | 10 μg/mL | 82.79 ± 3.83* |
| | 50 μg/mL | 111.39 ± 1.39 |
| | 100 μg/mL | 96.58 ± 1.06 |
| 0.6 N, 1 hour | 10 μg/mL | 80.88 ± 0.92** |
| | 50 μg/mL | 96.77 ± 0.12*** |
| | 100 μg/mL | 96.64 ± 0.88* |
| 1.2 N, 1 hour | 10 μg/mL | 73.89 ± 2.58*** |
| | 50 μg/mL | 109.34 ± 2.71*** |
| | 100 μg/mL | 114.77 ± 3.27*** |

Compared to the control group, *P < 0.05, P < 0.01, *P < 0.001.

Figure 12:
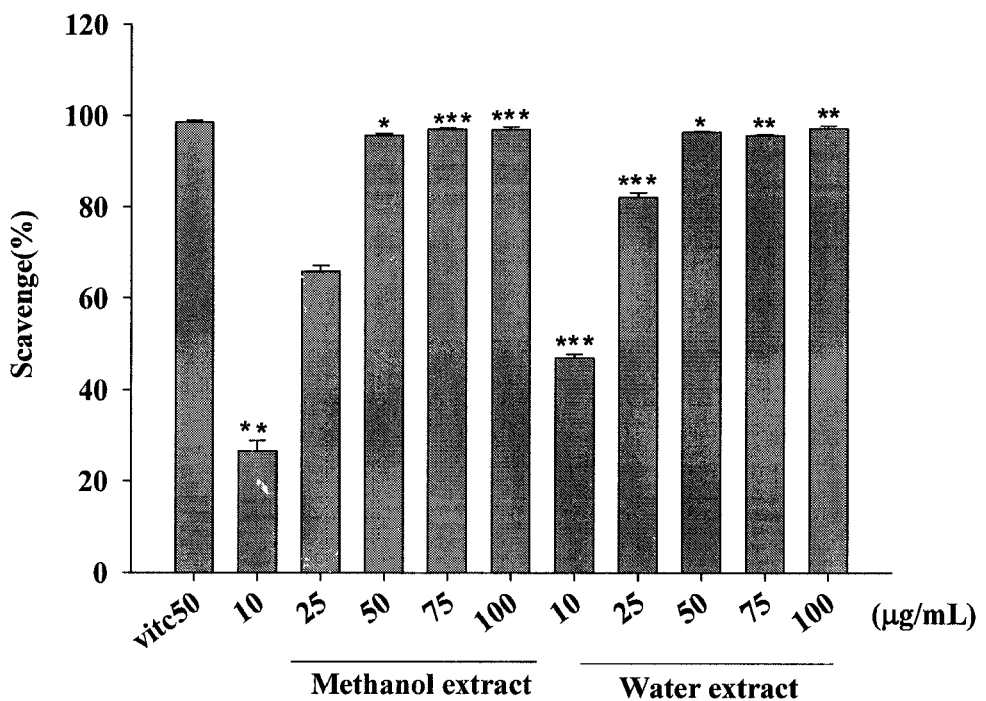
FIG. 12 is a bar diagram showing the scavenge rate of the *Neonauclea reticulata* leaf extract of the present invention on DPPH free radicals.
Figure 13:
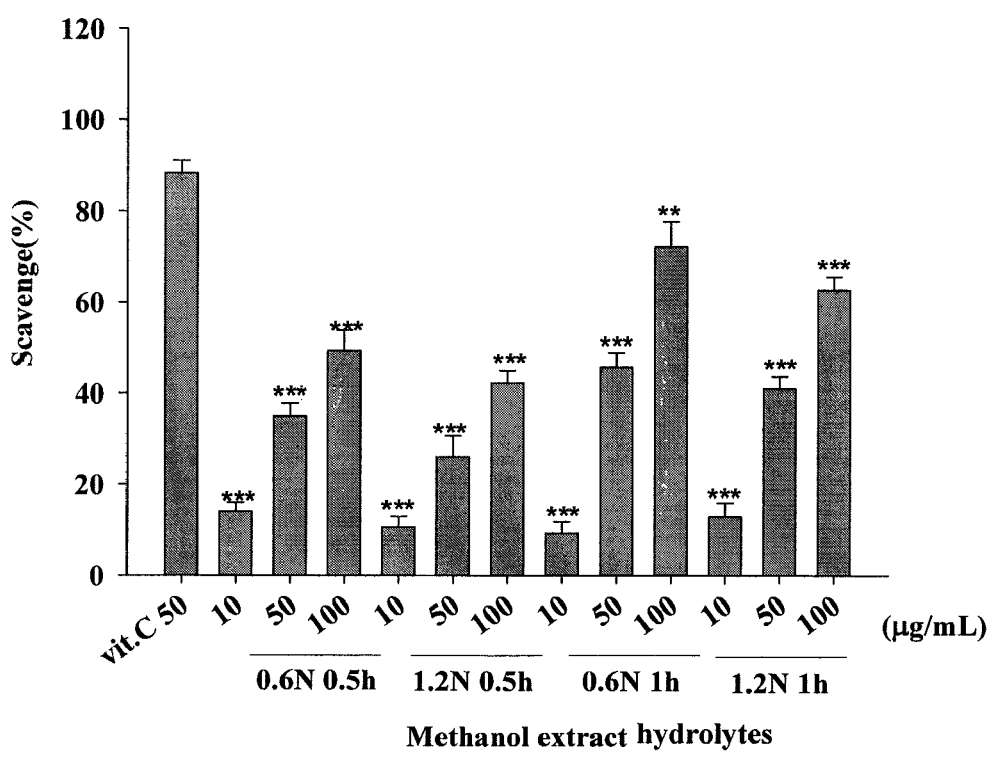
FIG. 13 is a bar diagram showing the scavenge rate of the hydrolyte of the *Neonauclea reticulata* leaf methanol extract of the present invention on DPPH free radicals.
Figure 14:
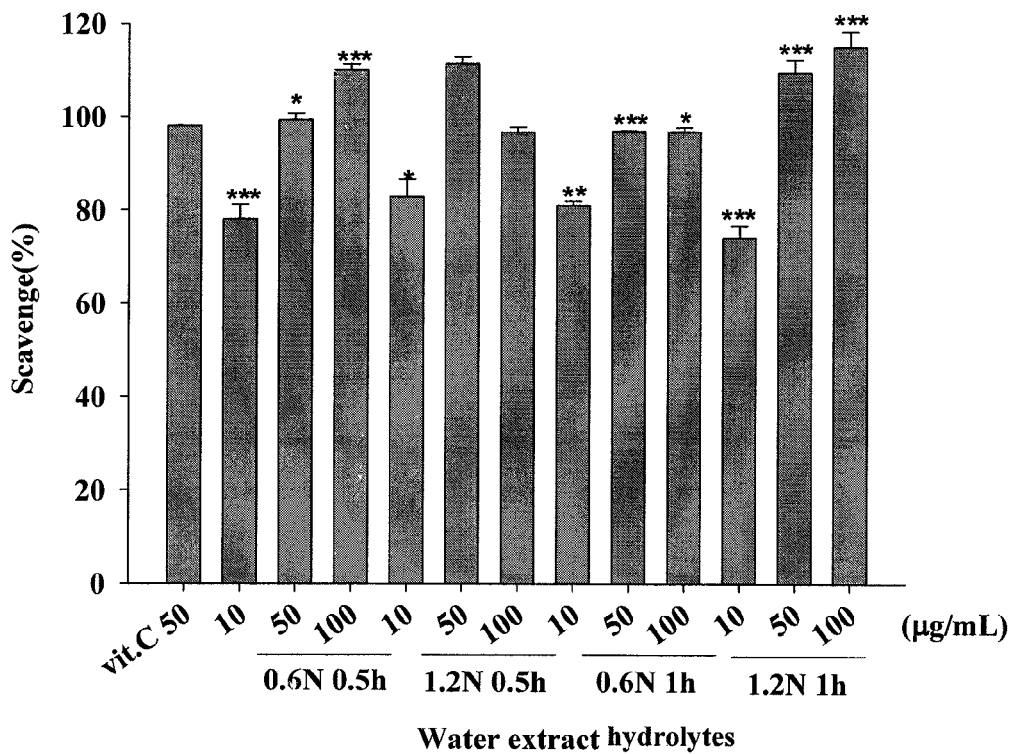
FIG. 14 is a bar diagram showing the scavenge rate of the hydrolyte of the *Neonauclea reticulata* leaf water extract of the present invention on DPPH free radicals.

As shown in Table 5 to Table 7 and FIG. 12 to FIG. 14, the DPPH free radical clearing/scavenging effect of the methanol extract and water extract of the *Neonauclea reticulata* leaves was concentration-dependant, and in the concentration of 50 μg/mL, the extracts had a similar scavenge effect as vitamin C. The hydrolyte of the methanol extract of the *Neonauclea reticulata* leaves under different reaction conditions can not inhibit the free radicals as effective as the extract itself. Under the concentration of 50 μg/mL, the hydrolyte of the water extract of the *Neonauclea reticulata* leaves under different reaction conditions had a similar scavenge efficiency as vitamin C.

This test showed that the methanol extract and water extract of the *Neonauclea reticulata* leaves and the hydrolyte thereof all have excellent anti-oxidation effect.

Experiment F. Anti-Oxidation Tests—Free Radicals Inhibition Tests

AAPH (2,2'-Azobis (2-methylpropionamidine)dihydrochloride) was used as the free radical source, and rat red blood cells were used to mimic a biomembrane to examine the ability of the *Neonauclea reticulata* leaf extract to protect biomembrane from the damage of free radicals. First, a moderate amount of blood from a rat was collected and placed into an eppendorf tube comprising heparin, and then a phosphate buffer solution (PBS) was added and mixed evenly. The samples were centrifuged at 3000×g for 15 minutes, and the supernatants were removed. After repeating the procedure for 5 times, 4 times weighted PBS was added to form a 20% red blood cell suspension. In an eppendorf tube, a 100 μL of the *Neonauclea reticulata* leaf water extract with different concentrations (0 to 500 μg/mL) was added into a solution containing 100 μL of a 20% red blood cell suspension and a 100 μL of an AAPH solution (300 mM), and mixed gently with a vibrator and reacted under 37° C. The samples were taken at a reaction time of 1, 1.5, 2, 3, and 4 hours (number of sample=3), and 300 μL of a phosphate buffer solution was added therein to terminate the reaction. Then, the samples were centrifuged at 3000×g for 2 minutes. A 200 μL of the supernatant was placed in a 96-well microplate, and the absorbance thereof was tested by an enzyme immunoassay instrument with a wavelength of 540 nm. The extract was replaced by the PBS as a control group, and the 20% red blood cell suspension was replaced by the PBS to determine the background value. The ability of the *Neonauclea reticulata* leaf extract to inhibit free radicals was calculated by the following formula, and the results are shown in Table 8 and FIG. 15.

$$\text{Inhibition Rate (\%)} = \left[\frac{\text{Absorption value of the control group} - \text{Absorption value of the experiment group}}{\text{Absorption value of the control group}}\right] \times 100$$

TABLE 8

| Group | 1.5 hour | 2 hour | 3 hour | 4 hour |
| --- | --- | --- | --- | --- |
| Water Extract 0 μg/mL | 0.00 ± 25.33 | −5.84 ± 48.92 | −9.19 ± 17.18 | −22.85 ± 14.25 |
| Water Extract 10 μg/mL | 7.41 ± 11.93 | 18.79 ± 8.62 | −0.42 ± 11.56 | −29.70 ± 24.48 |
| Water Extract 50 μg/mL | 70.02 ± 6.10 | 80.70 ± 6.92 | 61.06 ± 1.13 | 84.08 ± 4.26 |
| Water Extract 100 μg/mL | 85.18 ± 1.06 | 92.45 ± 1.13 | 88.61 ± 6.70 | 85.02 ± 5.38 |
| Water Extract 500 μg/mL | 84.16 ± 2.04 | 98.17 ± 0.97 | 99.51 ± 0.22 | 99.27 ± 0.23 |

Figure 15:
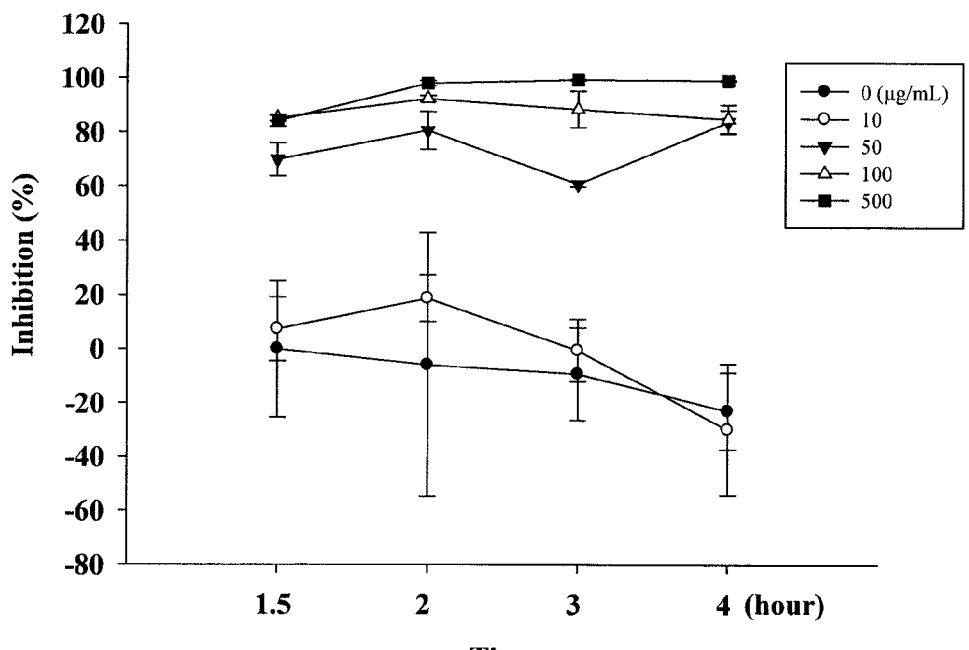
FIG. 15 is a curve diagram showing the inhibition rate of the *Neonauclea reticulata* leaf extract of the present invention on AAPH free radicals.

Table 8 and FIG. 15 showed that 4 hours later, the water extract of the *Neonauclea reticulata* leaf at the concentration of 50, 100, and 500 μg/mL can inhibit the AAPH to above 80%. This result showed that the *Neonauclea reticulata* leaf extract has an excellent anti-oxidation ability.

EXAMPLE 5

Experiment G Cytotoxicity Test

The cytotoxicity of the *Neonauclea reticulata* leaf extract was observed with an MTT (3-(4,5-dimethylthiazol-2-yl)-2,5-diphenyl tetrazolium bromide) assay. First, 50 μL of various concentrations (0 to 200 μg/mL) of the *Neonauclea reticulata* leaf extract was added into a 96-well culture plate that comprised fibroblast Hs68 ($10^4$ cells/well). After the cells were incubated in an incubator comprising 5 vol % carbon dioxide at 37° C. for 24 hours, 15 μL of an MTT solution (5 mg/mL, in PBS) was added into the well, and the fibroblasts were further incubated for 3 hours at 37° C. Then, 75 μL of a sodium dodecyl sulfate (SDS) solution (10% SDS, in 0.01 N HCl) was added into the culture plate, and the absorbance of each well was measured by an enzyme immunoassay instrument with a wavelength of 570 nm after 24 hours. Finally, the cell survival rate was calculated by the following formula, and the cytotoxicity of the extract was observed. The results are shown in Table 9 and FIG. 16.

$$\text{Cellular Survival Rate (\%)} = \left[\frac{\text{Absorption value of the experiment group}}{\text{Absorption value of the control group}}\right] \times 100$$

TABLE 9

| Group | Cellular Survival Rate (%) |
| --- | --- |
| Water Extract, 0 μg/mL | 100 ± 2.91 |
| Water Extract, 5 μg/mL | 99.57 ± 3.05 |
| Water Extract, 10 μg/mL | 102.81 ± 4.60 |
| Water Extract, 50 μg/mL | 108.01 ± 4.40*** |
| Water Extract, 100 μg/mL | 132.38 ± 5.43*** |
| Water Extract, 200 μg/mL | 154.35 ± 6.21*** |

Compared to the control group, ***$P < 0.05$.

Figure 16:
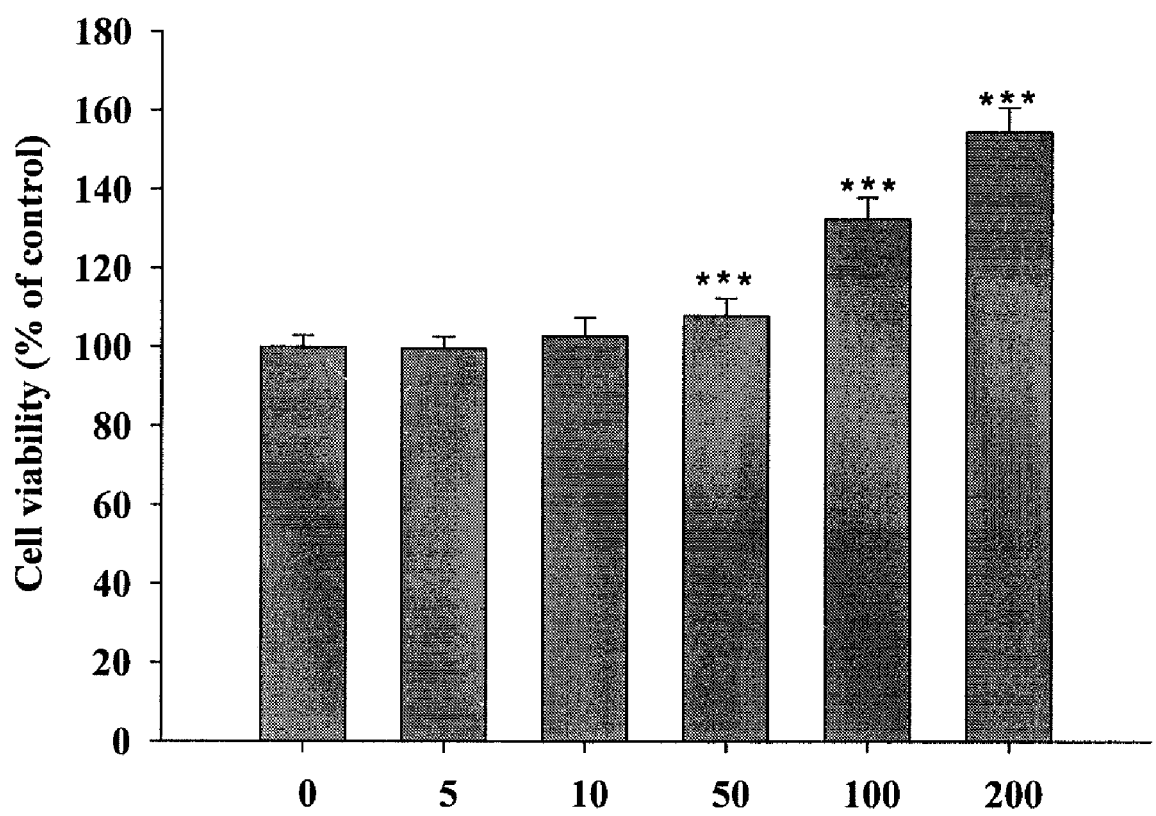
FIG. 16 is a bar diagram showing the cell viability of fibroblast Hs68.

Table 9 and FIG. 16 illustrated that the *Neonauclea reticulata* leaf water extract at the concentration of 0 to 200 μg/mL showed no cytotoxicity to fibroblasts Hs68, and when the concentration was higher than 50 μg/mL, it even had the effect of increasing the cellular survival rate.

According to the above tests, the *Neonauclea reticulata* leaf extract of the present invention has excellent effects of anti-oxidation, inhibiting the activity of matrix metalloproteinase, inhibiting the expression of matrix metalloproteinase, and/or inhibiting the phosphorylation of mitogen-activated protein kinase and is not cytotoxic. Therefore, the extract can achieve the effects of improving, repairing, and/or caring for skin without injuring the human body or animal.

The above disclosure is related to the detailed technical contents and inventive features Thereof. People skilled in this field may proceed with a variety of modifications and replacements based on the disclosures and suggestions of the invention as described without departing from the characteristics thereof. Nevertheless, although such modifications and replacements are not fully disclosed in the above descriptions, they have substantially been covered in the following claims as appended.

What is claimed is:

1. A method of inhibiting at least one selected from the group consisting of oxidation, the activity of matrix metalloproteinase (MMP), the expression of matrix metalloproteinase, and the phosphorylation of mitogen-activated protein kinase (MAP kinase) in a mammal, comprising administrating to the mammal an effective amount of a *Neonauclea reticulata* leaf extract, wherein the *Neonauclea reticulata* leaf extract is a water extract of *Neonauclea reticulata* leaf, a C1-C4 alcohol extract of *Neonauclea reticulata* leaf or a combination thereof.

2. The method as claimed in claim 1, wherein the absorption spectroscopy of the extract includes peaks within the following wavelength ranges: from 265 to 295 nm and from 305 to 335 nm.

3. The method as claimed in claim 1, wherein the absorption spectroscopy of the extract includes peaks within the following wavelength ranges: from 200 to 240 nm, from 245 to 255 nm, from 270 to 290 nm, and from 310 to 330 nm.

4. The method as claimed in claim 1, wherein the absorption spectroscopy of the extract includes peaks within the following wavelength ranges: from 200 to 240 nm, from 245 to 255 nm, from 270 to 290 nm, and from 310 to 330 nm and the extract is prepared by the following steps:
a) extracting *Neonauclea reticulata* leaves with a solvent and collecting the liquid phase; and
b) drying the collected liquid phase optionally,
wherein the solvent is selected from a group consisting of water, C1-C4 alcohols, and combinations thereof.

5. The method as claimed in claim 4, wherein the solvent is selected from a group consisting of water, methanol, ethanol, propanol, butanol, propylene glycol, and combinations thereof.

6. The method as claimed in claim 4, wherein the solvent is selected from a group consisting of water, methanol, and a combination thereof.

7. The method as claimed in claim 4, further comprising the following steps:
c) adding an acid into the liquid phase from step a) or the dried liquid phase from optional step b) to provide a mixture and maintaining the mixture at a temperature ranging from 70° C. to 90° C. to carry out a hydrolysis reaction;
d) partitioning the product from step c) with ethyl acetate and collecting the ethyl acetate layer; and
e) drying the collected ethyl acetate layer optionally.

8. The method as claimed in claim 7, wherein the acid is selected from a group consisting of hydrochloric acid, sulfuric acid, and a combination thereof

9. The method as claimed in claim 8, wherein the acid is hydrochloric acid with an equivalent concentration of 0.5 to 1.5.

10. The method as claimed in claim 1, wherein the matrix metalloproteinase is selected from a group consisting of matrix metalloproteinase-1 (MMP-1), matrix metalloproteinase-3 (MMP-3), matrix metalloproteinase-9 (MMP-9), and combinations thereof.

11. The method as claimed in claim 1, wherein the mitogen-activated protein kinase is selected from a group consisting of c-Jun N-terminal Kinase (JNK), extracellular signal-regulated protein kinase (ERK), p38 protein, and combinations thereof.

12. The method as claimed in claim 1, wherein at least one selected from the group consisting of improving skin, repairing skin, and caring for skin, occurs.

13. The method as claimed in claim 1, wherein photoaging is inhibited.

14. The method as claimed in claim 1, wherein photoaging induced by ultraviolet ray B (UVB) is inhibited.

15. The method as claimed in claim 1, wherein the extract is administrated as a medicament.

* * * * *